(12) United States Patent
Woods et al.

(10) Patent No.: US 8,603,098 B2
(45) Date of Patent: Dec. 10, 2013

(54) POSTERIOR MODULAR DISC REPLACEMENT SYSTEM

(75) Inventors: Richard W. Woods, Catonsville, MD (US); Hallett H. Mathews, Williamsburg, VA (US); Richard D. Guyer, Dallas, TX (US); Charles S. Theofolis, Palm Beach, FL (US); Gordon D. Donald, Fair Haven, NJ (US); Jean-Jaques Abitol, San Diego, CA (US)

(73) Assignee: K2M, Inc., Leesburg, VA (US)

(*) Notice: Subject to any disclaimer, the term of this patent is extended or adjusted under 35 U.S.C. 154(b) by 1547 days.

(21) Appl. No.: 11/518,419

(22) Filed: Sep. 11, 2006

(65) Prior Publication Data
US 2007/0129730 A1 Jun. 7, 2007

Related U.S. Application Data

(60) Provisional application No. 60/715,597, filed on Sep. 12, 2005.

(51) Int. Cl.
*A61B 17/56* (2006.01)
*A61F 2/44* (2006.01)

(52) U.S. Cl.
USPC .................. 606/99; 623/17.16; 623/17.11

(58) Field of Classification Search
USPC .................. 623/17.11–17.16; 606/90, 99
See application file for complete search history.

(56) References Cited

U.S. PATENT DOCUMENTS

| | | | | |
|---|---|---|---|---|
| 4,772,287 | A * | 9/1988 | Ray et al. | 623/17.12 |
| 4,904,260 | A * | 2/1990 | Ray et al. | 623/17.12 |
| 5,755,797 | A * | 5/1998 | Baumgartner | 623/17.16 |
| 6,387,130 | B1 * | 5/2002 | Stone et al. | 623/17.16 |
| 6,899,735 | B2 * | 5/2005 | Coates et al. | 623/17.16 |
| 2001/0016776 | A1 * | 8/2001 | Zuckerman et al. | 623/17.16 |
| 2002/0068975 | A1 * | 6/2002 | Teitelbaum et al. | 623/17.11 |
| 2003/0171812 | A1 * | 9/2003 | Grunberg et al. | 623/17.11 |
| 2003/0187445 | A1 * | 10/2003 | Keith et al. | 606/72 |
| 2004/0073313 | A1 * | 4/2004 | Link et al. | 623/17.15 |
| 2004/0102774 | A1 * | 5/2004 | Trieu | 606/61 |
| 2004/0167626 | A1 * | 8/2004 | Geremakis et al. | 623/17.15 |
| 2005/0171541 | A1 * | 8/2005 | Boehm et al. | 606/61 |
| 2007/0233245 | A1 * | 10/2007 | Trieu | 623/17.11 |
| 2008/0234687 | A1 * | 9/2008 | Schaller et al. | 606/90 |

\* cited by examiner

*Primary Examiner* — Kevin T Truong
*Assistant Examiner* — Christian Sevilla
(74) *Attorney, Agent, or Firm* — Carter, DeLuca, Farrell & Schmidt, LLP (57) ABSTRACT

Provided is a system and devices for use in the treatment and repair of moveable skeletal joints in the body of a subject. In particular, the present invention relates to the complete or partial posterior modular disc replacement of damaged or diseased fibrocartilage intervertebral discs in a subject wherein the replacement disc is capable of rotation and translation articulation.

26 Claims, 9 Drawing Sheets

POSTERIOR MODULAR DISC REPLACEMENT SYSTEM

BACKGROUND OF THE INVENTION

1. Field of the Invention

The present invention relates to devices, methods, and systems for the treatment and repair of moveable skeletal joints in the body of a subject. In particular, the present invention relates to the complete or partial replacement of diseased or damaged fibrocartilage components of the skeletal joints. More particularly, the present invention relates to complete or partial posterior modular disc replacement of damaged or diseased fibrocartilage intervertebral discs in a subject using a novel device and methods.

2. Background of the Technology

Mechanical back pain is the most common and costly musculoskeletal condition affecting middle-aged humans. Such back pain can be caused by several factors to include Degenerative Disc Disease.

Many devices have been invented for the purpose of stabilizing and/or replacing parts of the disc in an effort to ease the pain associated with disc disease. Many of the devices used and procedures necessary to install such devices in a patient have been extremely invasive requiring anterior access and exposure with resulting discomfort, unexpected complications, and prolonged recovery and pain. Examples of such devices and methods are found in U.S. Pat. No. 6,712,853 issued to Kuslich, U.S. Pat. No. 5,888,220 issued to Felt et al., U.S. Pat. No. 6,863,688 issued to Ralph et al., U.S. Pat. No. 6,887,272 issued to Ralph et al., and U.S. Pat. No. 6,899,735 issued to Coates et al.

While efforts to minimize the invasive nature of the procedure necessary to effect disc replacement have been made, such as U.S. Pat. No. 5,171,280 issued to Bumgartner, the resulting replacement disc has been less than satisfactory for the patients long term benefit. Thus a need exist for a system and method for providing a minimally invasive, effective, safe disc replacement.

SUMMARY OF THE INVENTION

The present invention provides a novel system for the repair or replacement of all or part of the fibrocartilage elements of the moveable skeletal joints in the body of a subject.

Also provided is a system and method of use for the complete or partial replacement of diseased or damaged fibrocartilage components of the skeletal joints.

Also provided is a system for posterior modular disc replacement for damaged or diseased fibrocartilage intervertebral discs in a subject.

Also provided is a method of using the assembly of the invention such that minimal time and effort is required to set the disc replacement device in the desired position relative to the anatomy of the subject.

Also provided is a kit that includes the assembly of the invention and surgical instruments necessary for placement of the device of the present invention in a subject.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description is provided as being exemplary of the invention, which may be embodied in various forms without departing from the scope of the claimed invention. Thus, the specific structural and functional details provided in the description of a posterior modular disc replacement are non-limiting, but serve merely as a basis for the invention defined by the claims provided herewith. The system as described below can be modified to provide replacement of joint components for other moveable skeletal joints in a subject without departing from the concept of the invention.

The present invention provides a system and a minimally invasive method for using the apparatus of the system to effect posterior modular disc replacement. The method and apparatus of the present invention is more easily and expeditiously accomplished with minimal risk and improved safety for the subject over conventional disc replacement apparatus and procedures.

Figure 1:
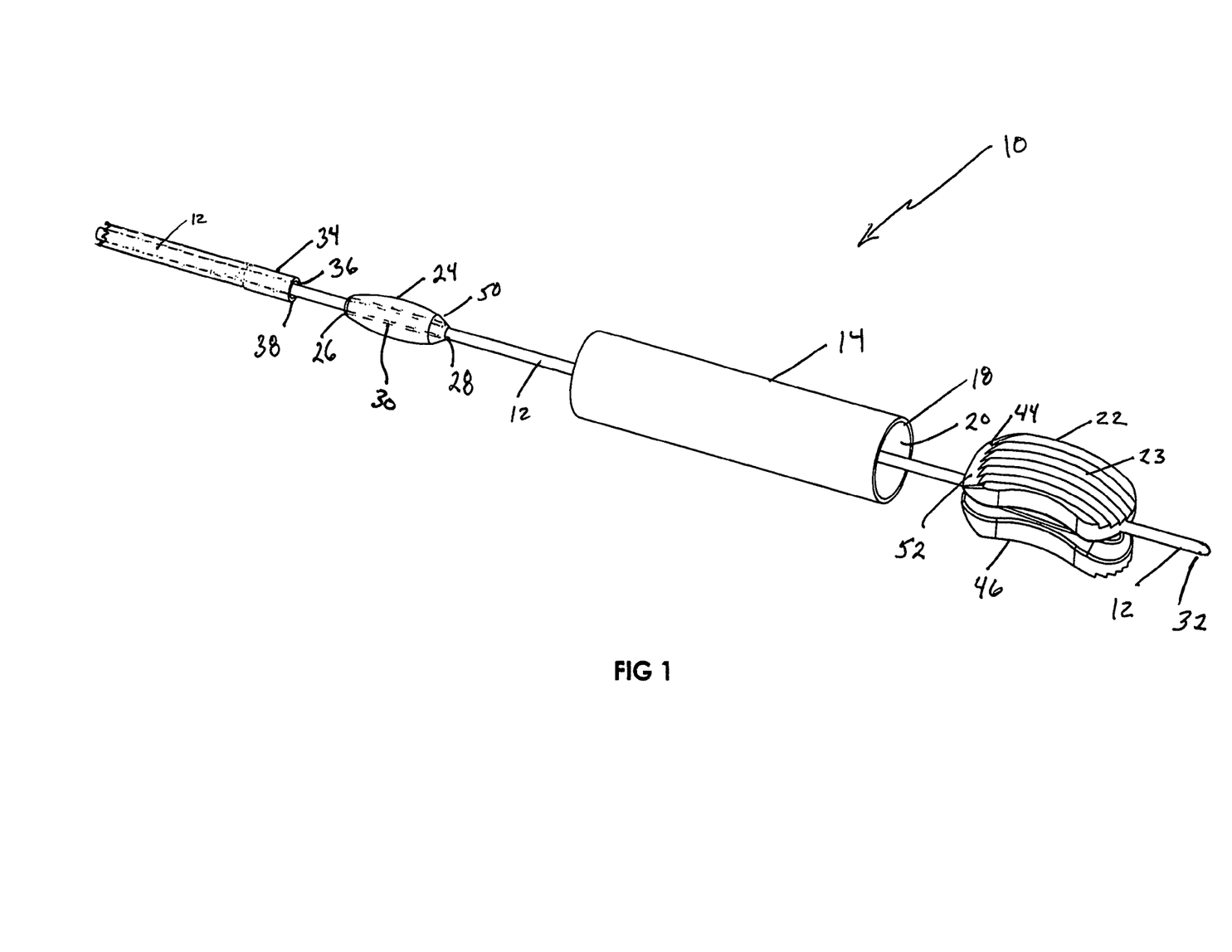
FIG. 1 provides a frontal perspective view of the one embodiment of the novel posterior modular disc replacement system of the present invention, showing the guide wire with a blunt tip, an end plate in the closed configuration inserted over on the guide wire, an insertion cannula through which the guide wire is slidably passed, a spreader bearing inserted over the guide wire, and an insertion tool threaded on the guide wire, FIG. 2A-B provides a frontal and side view of the novel end plate element of the present invention in a closed configuration, FIG. 3A-B provides a frontal and side view of the end plate of the present invention in a spread configuration with the spreader bearing inserted therein, FIG. 4 provides a frontal perspective view of the end plate of the present invention in a spread configuration with the spreader bearing inserted therein, FIG. 5 provides a cross-sectional frontal view of an alternative embodiment of the system of the present invention having an at least partially threaded guide wire, at least one locking element configured to be releasably locked on the guide wire, and a spacer element configured to be positioned between two end plates, FIG. 6 provides a side view of an alternative guide wire of the present invention having a spherical head element, FIG. 7 provides a side view of an alternative guide wire assembly of the present invention having a first and a second guide wire that can be releasably attached one to the other, FIG. 8 provides a perspective view of a guide wire slidably passed through an end plate of the present invention in a closed position, wherein the end plate is releasably held in the closed position by at least one banding element, FIG. 9A provides a top view of a vertebra and shows a properly positioned guide wire of the present invention as well as the alternative embodiment of having a guide wire assembly of a first and second guidewire that can be releasably attached one to the other.
Figure 5:
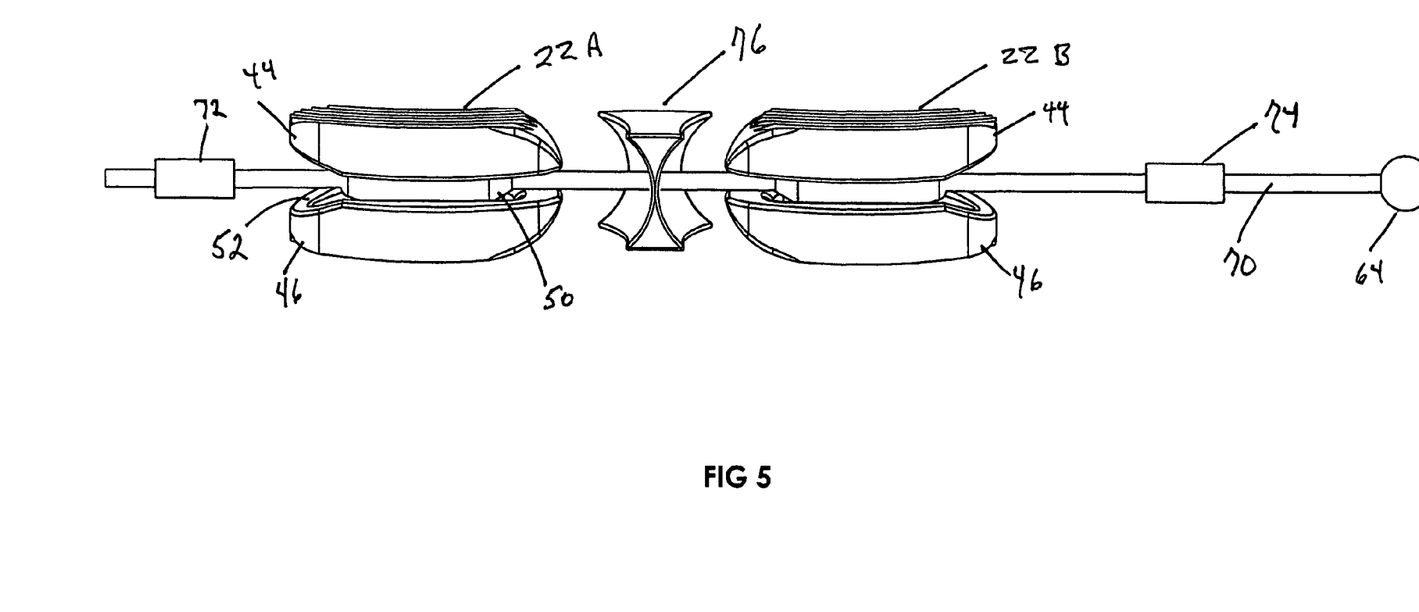
Figure 6:
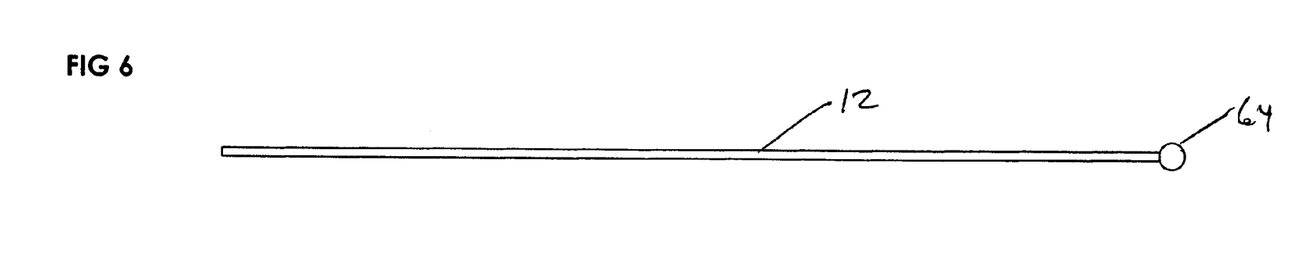
Figure 7:
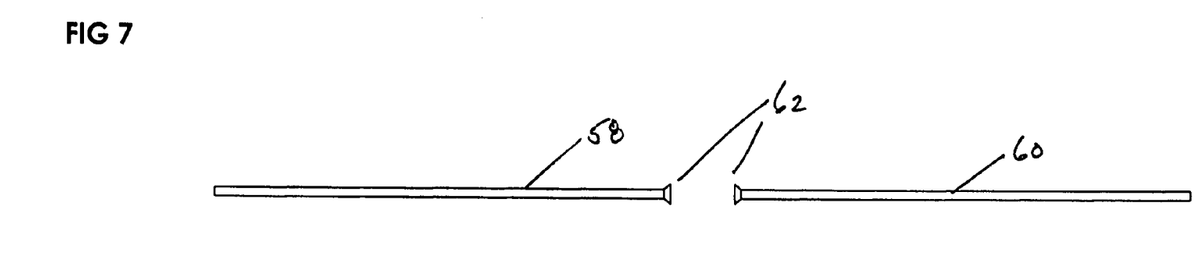

With reference to FIGS. 1-10V, the present invention is a novel posterior modular disc replacement system. As best shown in FIG. 1 the system, generally shown at 10, includes a guide wire 12, an insertion cannula 14, having a first cannula opening 16 and a second cannula opening 18 connected one to the other by a cannula lumen 20, which is sized and configured to allow easy passage of the guide wire 12 along the cannula longitudinal axis. Also included in the system of the present invention is at least one end plate 22, which is sized and configured so as to be capable of passage over the guide wire 12 and through the lumen 20 of the insertion cannula 14. A spreader bearing 24, is sized and configured to be capable of passage over the guide wire 12 and through the lumen 20 of the insertion cannula 14. The spreader bearing 24 can include a first and second guide wire portal 26, 28, which are respectively disposed at opposing ends of the spreader bearing 24 and are connected by a spreader bearing lumen 30, which is sized so as to permit the spreader bearing 24 to pass over the guide wire 12. The guide wire 12 can terminate at the insertion end with a blunt tip 32, as shown in FIG. 1 or alternatively with a spherical guide wire head 64 as best shown in FIGS. 5, 6, and 9A. An insertion tool 34 is configured for manual control by a user and is provided with an insertion tool lumen 36, which extends along the longitudinal axis of the insertion tool terminating at each end in an first and second external opening 40, 42.

Figure 9A:
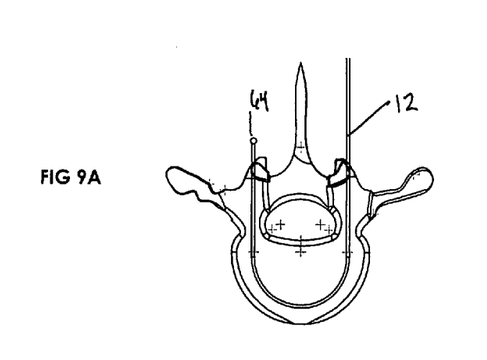
Figure 9B:
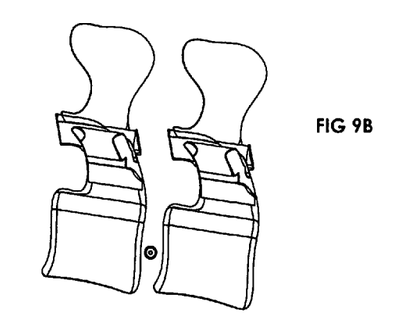
FIG. 9B shows a side view of two adjacent vertebral bodies and the relative position of an insertion cannula and guide wire of the present invention.
Figure 9C:
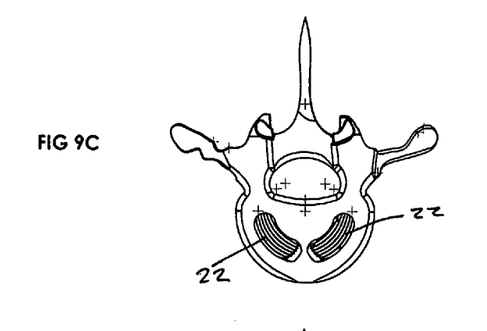
FIG. 9C shows a top view of a vertebra having two end plates in closed configuration positioned adjacent thereto and FIG. 9D shows a side view of the end plates in a closed configuration relative to two adjacent vertebral bodies.
Figure 9D:
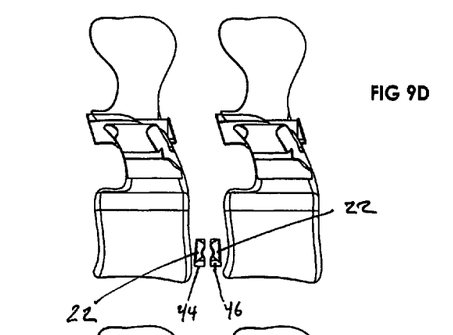
Figure 9E:
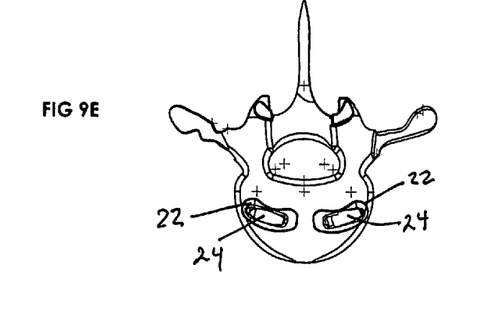
FIG. 9E-F shows a top and side view of vertebra with two end plates in a spread configuration with each containing a respective spreader bearing, FIG. 10A-V provides a series of views of a vertebra having the assembly of the present invention and elements thereof positioned relative to the vertebra to demonstrate the sequential operation of the present invention with FIGS. 10G and 10I showing an alternative embodiment of an insertion cannula with a guide wire scooping element for directing the path of a guidewire.
Figure 9F:
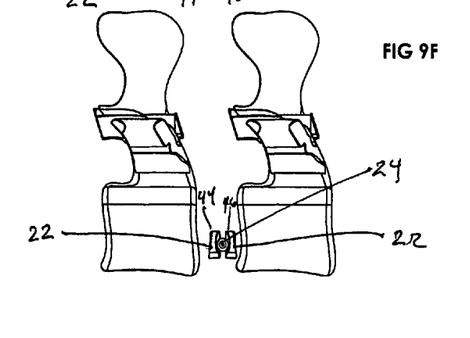

In practice, as best demonstrated in FIGS. 9A-F and FIGS. 10A-V, the guide wire is inserted between two adjacent vertebra so as to be properly positioned to facilitate a posterior modular disc replacement. As best shown in FIG. 10C-F, the guide wire can be biased to facilitate the user's movement of the guidewire in the desired direction. As shown in FIG. 9A, the guide wire 12 placement can be accomplished using one guide wire or alternative by using a first and second guide wire component 58, 60 that can be releasably connected one to the other at a guide wire attachment point 62. Any releaseable attachment mechanism such as quick release, bayonet fitting, leur-lock type, or other screw-type fitting can be used as a releaseable attachment mechanism. As illustrated in FIGS. 9C-D, one or more (preferably two) end plates 22 in a closed configuration can be threaded along the guide wire 12 into the desired position to effect posterior modular disc replacement. Once the end plate 22 is in position, a spreader bearing 24 can be threaded along the guide wire and positioned withing the end plate 22 as best shown in FIGS. 9E-F. Once positioned and in a spread configuration, the end plates 22 of the present invention provide a minimally invasive, safe, and effective posterior modular disc replacement.

Figure 2A:
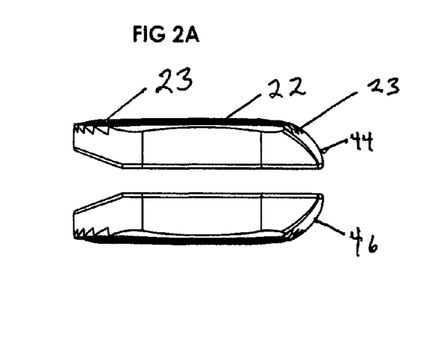
Figure 2B:
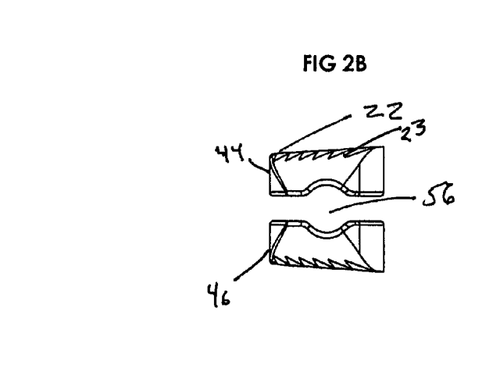
Figure 3A:
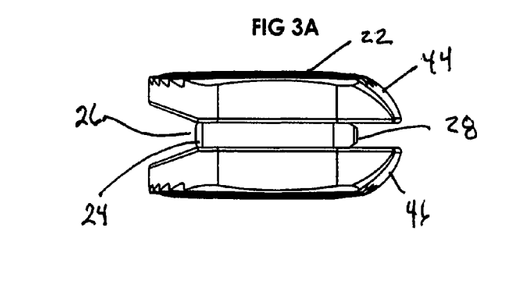
Figure 3B:
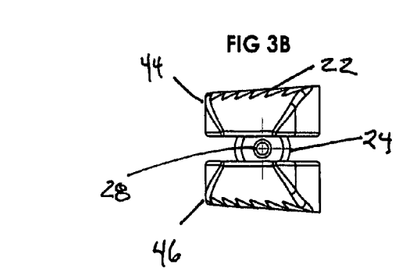
Figure 4:
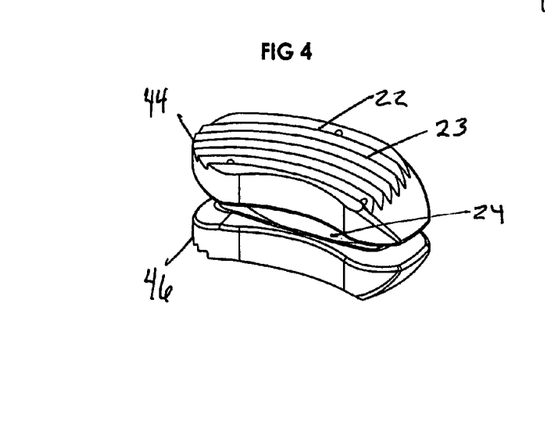

To attain effective, safe disc replacement, the novel system of the present invention provides each of the system elements shown in FIG. 1. The system of the present invention can be employed as described above and illustrated in FIGS. 9A-F and FIGS. 10A-V. The ability of the system of the present invention to easily move the components into position and then secure the replacement disc into a proper position is central to the present invention advantages. As best shown in FIG. 2A-B, the novel end plate 22 of the present invention is configured as having a first and a second end plate opposing body 44, 46, which may or not be virtual mirror-images. The exterior of the end plate 22 can incorporate gripping elements such as a textured, ridged, or ribbed surface as an aid to maintaining good contact and relative position to the vertebral body. The opposing bodies 44, 46 of the end plate 22 can be connected one to the other or can be held in relative position, one to the other, by a variety of means. For example, the opposing bodies 44, 46 can be connected along one or more edges by a break-away joint 48, which is composed of such material as to permit the opposing bodies 44, 46 to be separated one from the other with a predetermined amount of mechanical force. Importantly, the breakaway joint should be of sufficient strength to retain the opposing bodies in relative position one to the other until the user of the system elects to forcibly fracture the breakaway joint 48 by manual application of force. It is within the concept of the invention that the breakaway joint can alternatively be broken chemically, thermally, photolytically, or by other means known for disassociating two portions one from the other. The manual exertion of force to fracture the breakaway joint is accomplished by the user employing the insertion tool to physically move the spreader bearing 24 along the guide wire 12 to the point that it makes contact with the end plate 22. The relative contact points of the spreader bearing 24 and the end plate 22 are relatively complementary one to the other, such as for example, a convex surface 50 on the end of the spreader bearing 24 abutting against a concave surface 52 on the end of the end plate 22. In operation, when the convex surface 50 of the end of spreader bearing 24 is manually forced against the concave surface 52 of the end plate 22, the first and second opposing bodies 44, 46 of the end plate 22 are forced apart. This act of manually forcing apart the opposing bodies 44, 46 serves to alter the configuration of the end plate from a closed configuration to a spread configuration. The surfaces of the opposing bodies 44, 46, which directly oppose each other are configured to define a spreader bearing seat 56, which may or may not resemble a concavity. As the opposing bodies 44, 46 of the end plate 22 are moved into the spread configuration, as best shown in FIGS. 3A-3B, the spreader bearing 24 is positioned in the spreader bearing seat 56 so as to securely hold the end plate in the spread configuration. In the spread configuration, the end plate 22 is securely butted against the opposing surfaces of the two adjacent vertebra thus providing a secure, effective disc replacement. As the gripping elements 23 of the opposing bodies 44, 46 provide a secure contact with the bone surface, the spreader bearing 24 positioned within the spreader bearing seat provides an articulation surface between the opposing inner surfaces of the two opposing bodies 44, 46. The end plate thus provides a securely seated modular disc replacement capable of rotation and translation.

Figure 8:
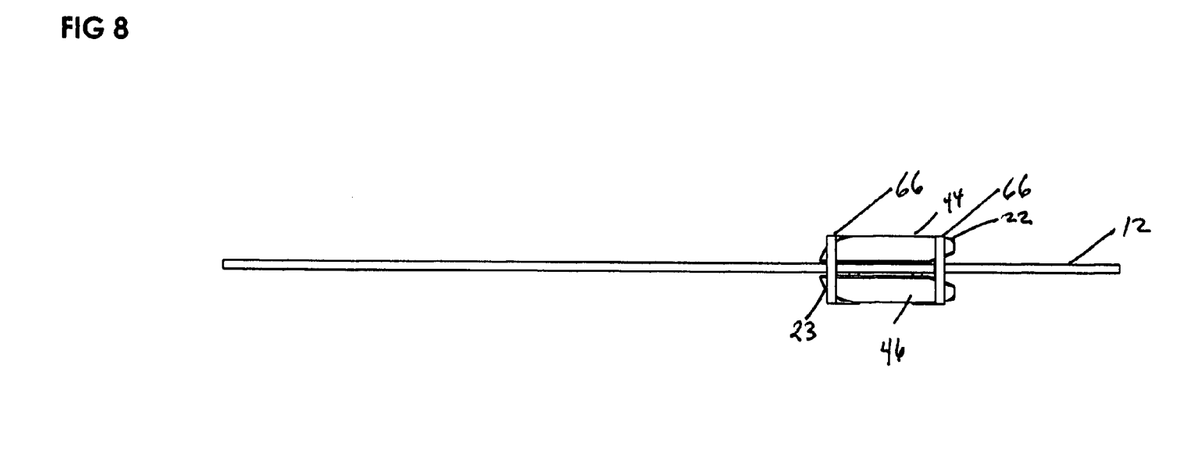

Additional embodiments of the present invention are within the concept of the invention and can be employed as the user finds advantageous to the circumstance. Alternative guide wire heads, such as, for example, the spherical guide wire head 64 best shown in FIGS. 5, 6, and 9A can be employed if needed to more easily pass through the soft tissues of a subject. Other alternative embodiments, such as releasably securing the opposing bodies 44, 46 one to the other can include the use of at least one banding element 66. The banding element, as best shown in FIG. 8, can be of an elastic nature and can remain in place after the user has employed the insertion tool 34 to force the spreading bearing 24 into the spreader bearing seat 56. Alternatively, if employed, the banding element 66 can be composed of a material that fractures when the user applies force to the system to open the end plate 22 into a spread configuration or the banding element 66 can be composed of a material that initially stretches to permit movement of the opposing bodies 44, 46 away from each other and subsequently is adsorbed or dissolved naturally in the body of the subject. The modification of the system to include any such alternative still lies within the concept of the invention.

Figure 10A:
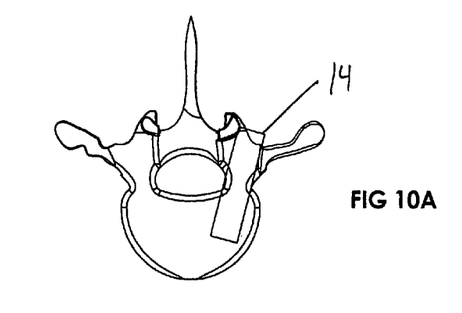
Figure 10B:
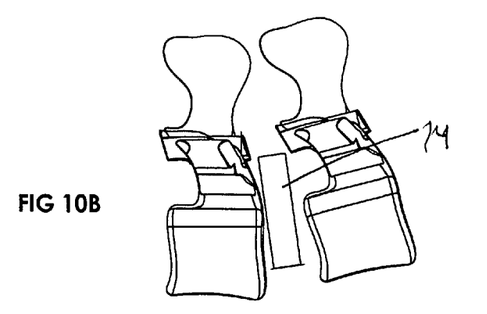
Figure 10C:
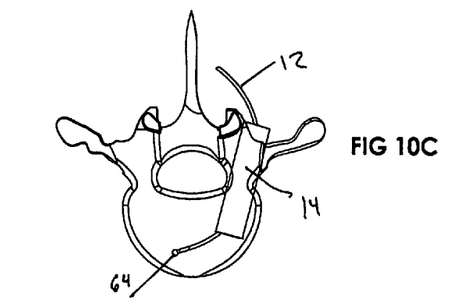
Figure 10D:
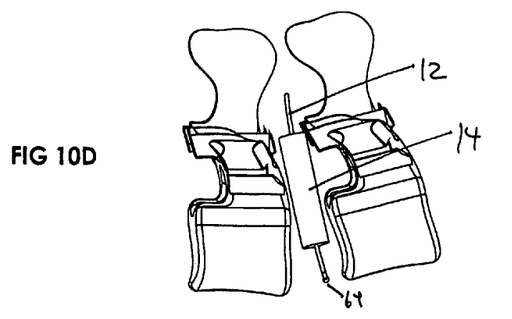
Figure 10E:
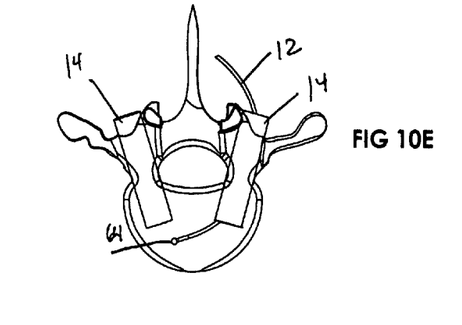
Figure 10F:
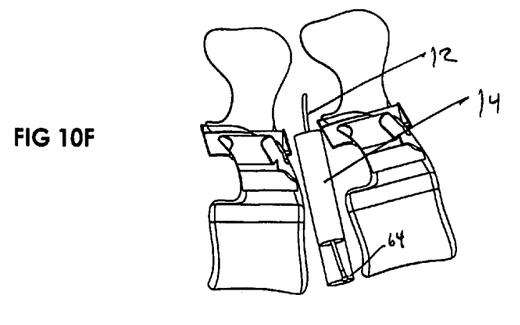
Figure 10G:
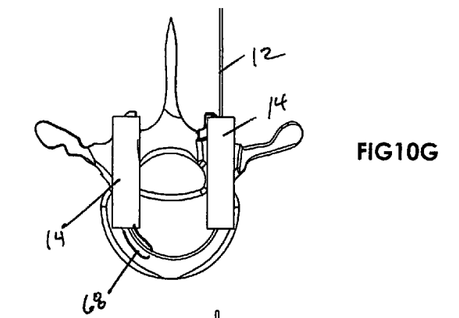
Figure 10H:
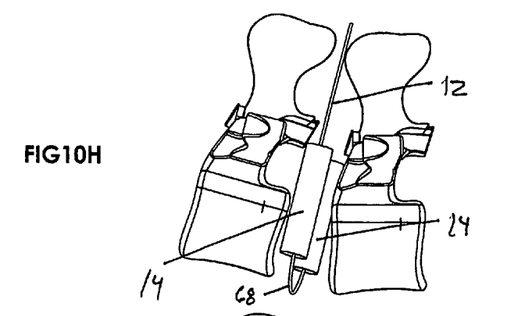
Figure 10I:
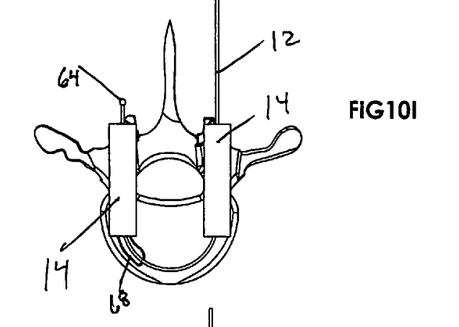
Figure 10J:
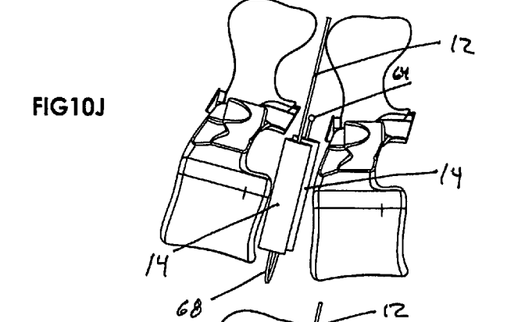
Figure 10K:
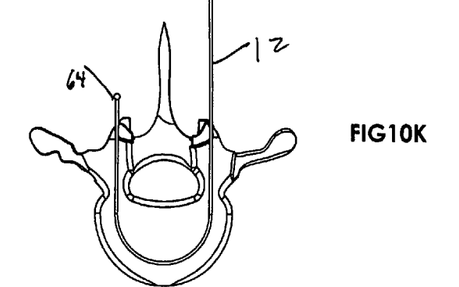
Figure 10L:
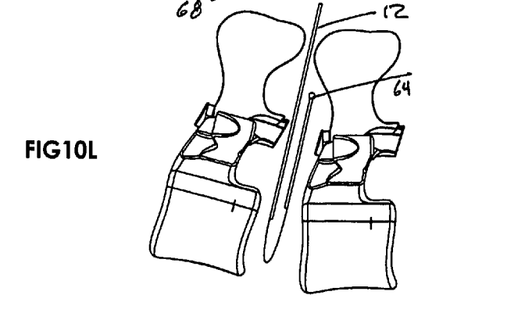
Figure 10M:
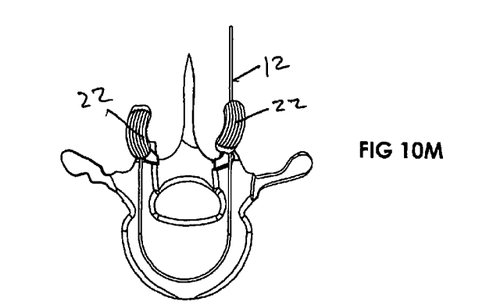
Figure 10N:
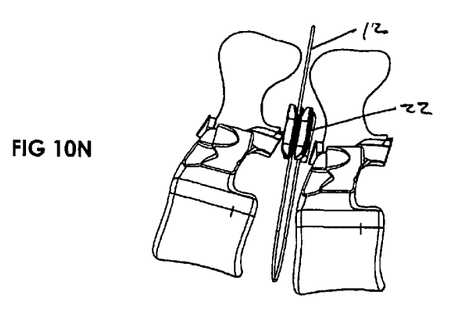
Figure 10O:
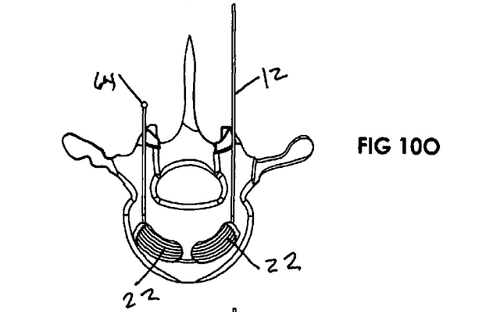
Figure 10P:
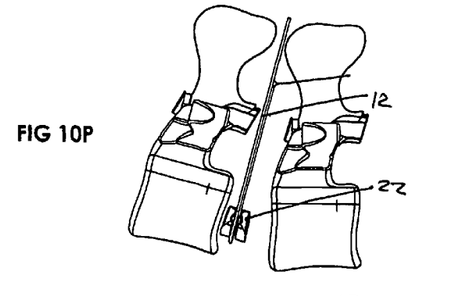
Figure 10Q:
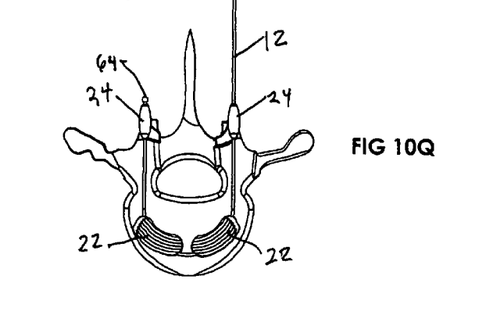
Figure 10R:
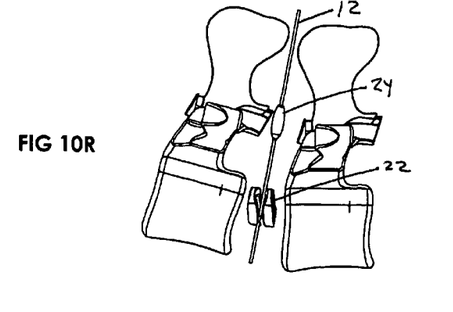
Figures 10S, 10U:
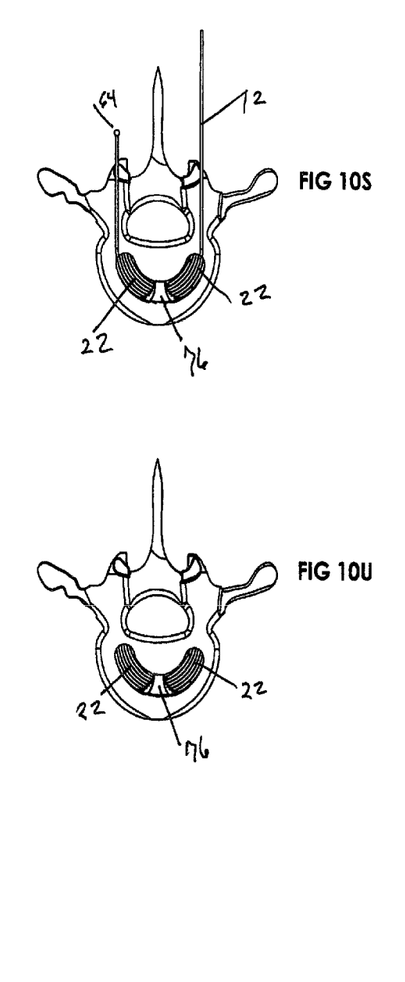
Figure 10T:
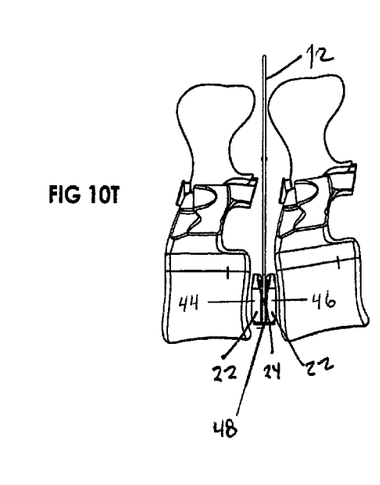
Figure 10V:
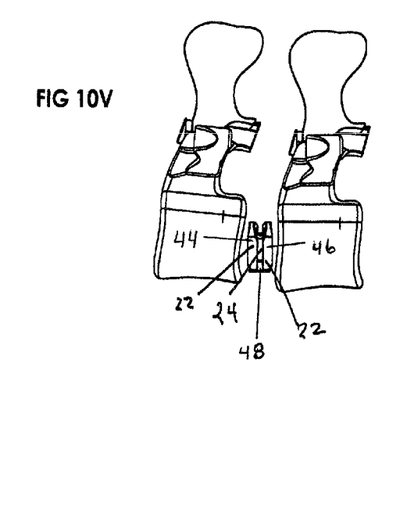

The practice of the sequential steps of method of using the invention are well illustrated in FIGS. 10A-V. The use of an alternative insertion cannula element having a guide wire scoop 68 is best illustrated in FIGS. 10G and 10I. Advantageously, the lower portion of the insertion cannula 68 can be modified to include an open scoop-shaped portion that can serve to guide the blunt end 32 of the guide wire 24 into the lumen of the cannula. While the illustration shows the guide wire scoop 68 being useful in directing guide wire 12 back out of the body, it is within the scope of the invention to use such an alternative cannula with a scoop for guide wire insertion also.

Another alternative embodiment, as best shown in FIG. 5, includes the use of an alternative guide wire 70 that is at least partially threaded. For use with such a guide wire, one or more, and preferably two releaseable locking elements 72, 74 can be employed at the outlying portions of the guidewire to hold the assembly of end plates 22 in relative position to each other. As shown in FIG. 5, an end plate spacer element 76 can be threaded along the guide wire as with other elements of the system and positioned between two end plates 22A, 22B. In such an alternative embodiment, the locking elements also serve to hold the spacer 76 securely between the two end plates 22A, 22B and the portion of the guide wire, which is threadably secured by the locking elements 72, 74 would remain in the subject after the procedure. It is also within the concept of the invention to also employ the spacer 76 between two end plates as demonstrated in FIGS. 10S and 10U.

Materials and manufacturing procedures as are well known in the art can be employed in the preparation of the invention.

Each of the embodiments described above are provided for illustrative purposes only and it is within the concept of the invention to include modifications and varying configurations without departing from the scope of the invention that is limited only by the claims included herewith.

What is claimed is:

1. A system for posterior modular disc replacement, comprising:
   a first guide wire,
   an insertion cannula having a through lumen through which said first guide wire is capable of slidably passing,
   at least one end plate element that is capable of slidably passing circumferentially along the length of said first guide wire and is sized and configured to slidably pass through said lumen, said end plate comprising at least two opposing bodies adjacent one to the other, said adjacent opposing bodies being capable of physically separating one from the other,
   at least one spreader bearing that is capable of slidably passing circumferentially along the length of said first guide wire and is sized and configured to slidably pass through said lumen, said bearing also being sized and configured to be inserted between said opposing bodies to urge said opposing bodies apart from one another, and
   at least one banding element positioned around said opposing bodies to hold said opposing bodies in relative position one to the other.

2. The system of claim 1, wherein said spreader bearing is capable of effecting the spreading apart and physical separation of said opposing bodies relative to each other.

3. The system of claim 2, further comprising at least one insertion tool that is sized and configured to pass along said first guide wire so as to make forceful contact with said spreader bearing,
   whereby said spreader bearing can be forced into a position between said opposing bodies so as to effect the spreading apart of said opposing bodies one from the other.

4. The system of claim 1, further comprising at least one locking element sized and configured to slidably pass circumferentially over said first guide wire, said at least one locking element being capable of being selectively secured to said first guide wire.

5. The system of claim 4, wherein said at least one locking element can be selectively released from a locked position on said first guide wire.

6. The system of claim 1 wherein said at least one banding element is elastic and capable of allowing movement of said opposing bodies away from each other when force is applied to said opposing bodies through said spreader bearing.

7. The system of claim 1, wherein said at least one banding element is capable of fracturing and allowing movement of said opposing bodies away from each other when force is applied to said opposing bodies through said spreader bearing.

8. The system of claim 1, wherein said at least one banding element is bio-absorbable after said opposing bodies have been spread apart one from the other.

9. The system of claim 1, further comprising a second guide wire, said second guide wire being capable of insertion from an opposing direction to said first guide wire and being configured for connection to said first guide wire.

10. The system of claim 9, wherein said connection of said first guide wire to said second guide wire is a connection type selected from the group consisting of quick release, bayonet fitting, luer-lock, and screw-type fitting.

11. The system of claim 9, wherein said connection of first and second guide wires is a releasable attachment.

12. The system of claim 1, further comprising a scooping element sized and configured to be inserted from the opposite direction of said first guide wire and configured to receive a terminal end of said first guide wire during an insertion process and direct a path of said first guide wire.

13. The system of claim 12, wherein said terminal end of said first guide wire is a blunt end.

14. The system of claim 1, comprising two end plate elements, each of said end plate elements being aligned sequentially along said first guide wire.

15. The system of claim 13, wherein said two end plates are separated one from the other by an end plate spacer element.

16. A device for replacing all or a portion of fibrocartilage tissue with a moveable joint of a subject, comprising:
   a guide wire,
   at least one end plate element that is capable of slidably passing circumferentially along the length of said guide wire and is sized and configured for placement within a moveable joint space of a subject, said end plate comprising at least two opposing bodies adjacent one to the other, said adjacent opposing bodies being capable of physically separating one from the other,
   at least one spreader bearing configured to slidably pass circumferentially along the length of said guide wire, the at least one spreader bearing sized and configured to be inserted between said opposing bodies to urge said opposing bodies apart from one another, and
   at least one banding element positioned around said opposing bodies to hold said opposing bodies in relative position one to the other.

17. The device of claim 16, wherein said spreader bearing provides an articulation surface between the opposing inner surfaces of said opposing bodies.

18. The device of claim 17, wherein said opposing bodies are capable of rotational and translational articulation relative to each other.

19. The device of claim 16, wherein said spreader bearing is sized and configured to effect a spreading apart and physical separation of said opposing bodies one from the other.

20. The device of claim 16, wherein said opposing bodies comprise gripping elements on the respective outer surfaces of said opposing bodies, said gripping elements being capable of providing a secure contact with adjacent vertebral bone material.

21. The device of claim 16, wherein said fibrocartilage tissue is an intervertebral disc.

22. The device of claim 16, wherein said at least one banding element is capable of fracturing and allowing movement of said opposing bodies away from each other when force is applied to said opposing bodies through said spreader bearing.

23. The device of claim 16, wherein said at least one banding element is bio absorbable after said opposing bodies have been spread apart one from the other.

24. A method of using the system of claim 1, the method comprising:
  positioning said guide wire in a joint space of a moveable joint of a subject,
  slidably moving said at least one end plate along said guide wire into a desired position with said joint space,
  slidably moving said at least one spreader bearing along said guide wire until said spreader bearing makes contact with said end plate and effects the spreading apart and physical separation of two opposing bodies of said end plate relative one to the other,
  removing said guide wire.

25. A kit for use in a surgical procedure, said kit comprising:
  a guide wire,
  an insertion cannula having a through lumen along its longitudinal axis through which said guide wire is capable of slidably passing,
  at least one end plate element that is capable of slidably passing circumferentially along the length of said guide wire and is sized and configured to slidably pass through the lumen of said insertion cannula, said end plate comprising at least two opposing bodies adjacent one to the other, said two opposing bodies being capable of being physically separated one from the other,
  at least one spreader bearing that is capable of slidably passing circumferentially along the length of said guide wire and is sized and configured to slidably pass through the lumen of said insertion cannula, said bearing also being sized and configured to be forcefully inserted between said opposing bodies so as to effect the spreading apart of said opposing bodies relative to each other, and
  at least one banding element positioned around said opposing bodies to hold said opposing bodies in relative position one to the other.

26. The kit of claim 25, further comprising at least one insertion tool that can be manually operated and is sized and configured to pass along said guide wire so as to make forceful contact with said spreader bearing, and a sealable packaging container.

* * * * *